US012733659B2

(12) United States Patent
Kim et al.

(10) Patent No.: US 12,733,659 B2
(45) Date of Patent: Sep. 15, 2026

(54) GRYLLUS BIMACULATUS EXTRACT AND METHOD FOR PREPARING THE SAME

(71) Applicant: CJ CHEILJEDANG CORPORATION, Jung-gu (KR)

(72) Inventors: Yeo Jin Kim, Seongdong-gu (KR); Dong Joo Shin, Seocho-gu (KR); Su Jin Bae, Suwon-si (KR); Hyung Cheol Kim, Yongin-si (KR); Hong Wook Park, Gangnam-gu (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 903 days.

(21) Appl. No.: 17/298,188

(22) PCT Filed: Oct. 31, 2019

(86) PCT No.: PCT/KR2019/014646
§ 371 (c)(1),
(2) Date: May 28, 2021

(87) PCT Pub. No.: WO2020/091483
PCT Pub. Date: May 7, 2020

(65) Prior Publication Data

US 2022/0279813 A1 Sep. 8, 2022

(30) Foreign Application Priority Data

Oct. 31, 2018 (KR) ........................ 10-2018-0132419

(51) Int. Cl.
*A23J 1/02* (2006.01)
*A23J 3/04* (2006.01)
*A23L 33/17* (2016.01)
*C12N 9/54* (2006.01)
*C12P 21/06* (2006.01)

(52) U.S. Cl.
CPC .................. *A23J 1/02* (2013.01); *A23J 3/04* (2013.01); *A23L 33/17* (2016.08); *C12N 9/54* (2013.01); *C12P 21/06* (2013.01); *A23V 2002/00* (2013.01)

(58) Field of Classification Search
CPC .............. A23L 33/17; A23J 3/04; C12P 21/06
See application file for complete search history.

(56) References Cited

U.S. PATENT DOCUMENTS

2017/0165195 A1 6/2017 Lee
2018/0002452 A1* 1/2018 Berezina ................ C12P 19/26
2018/0317520 A1 11/2018 Bouzari et al.
(Continued)

FOREIGN PATENT DOCUMENTS

JP 2006-342153 A 12/2006
JP 2009-254348 A 11/2009
KR 10-1999-0058644 A 7/1999
(Continued)

OTHER PUBLICATIONS

Bong et al. KR 20160134939 A English Translation. (Year: 2016).*
(Continued)

*Primary Examiner* — Stephanie A Kohler
(74) *Attorney, Agent, or Firm* — Morgan, Lewis & Bockius LLP

(57) ABSTRACT

The present application relates to a *Gryllus bimaculatus* extract and a method for preparing the same.

11 Claims, 7 Drawing Sheets

(56) References Cited

U.S. PATENT DOCUMENTS

| | | | |
|---|---|---|---|
| 2019/0374459 A1 | 12/2019 | Lee | |

FOREIGN PATENT DOCUMENTS

| | | | |
|---|---|---|---|
| KR | 10-1200404 B1 | 11/2012 | |
| KR | 10-2016-0134939 A | 11/2016 | |
| KR | 10-2017-0014448 A | 2/2017 | |
| KR | 10-1702851 B1 | 2/2017 | |
| KR | 10-2018-0114680 A | 10/2018 | |
| WO | WO-2016108034 A1 * | 7/2016 | ....... C07K 14/43563 |
| WO | 2017/079427 A1 | 5/2017 | |

OTHER PUBLICATIONS

Derwent Abstract of Park (KR 20170014448 A). (Year: 2017).*

Notice of Allowance issued on Aug. 29, 2023 for the corresponding Korean patent application 10-2019-0138132 (7 pages).

Dong-Gue Lee et al., "Quality Characteristics of Two-spotted Cricket (*Gryllus bimaculatus*) Brown Stock by High Pressure Cooking", Culinary Science & Hospitality Research, vol. 23, No. 4, Jun. 30, 2017, pp. 163-174.

Office Action issued in corresponding Korean Patent Application No. 2019-0138132, mailed Jun. 28, 2021, 7 pages.

Author Unknown, "A Base Study for Certification of cricket originated food ingredients", National Institute of Agricultural Sciences, 2016, pp. 1-235, Project No. PJ009827 (with English Abstract).

Extended European Search Report for EP Application No. 19879425.7 mailed Jul. 11, 2022 (8 pages).

Hall et al., "Functional properties of tropical banded cricket (*Gryllodes sigillatus*) protein hydrolysates", Food Chemistry, Elsevier Ltd, NL, vol. 224, 2016, pp. 414-422, XP029904876, ISSN: 0308-8146, DOI: 10.1016/J.Foodchem.2016.11.138.

International Search Report for International Patent Application No. PCT/KR2019/014646 mailed Feb. 21, 2020, 5 pages.

Written Opinion of the International Searching Authority for International Patent Application No. PCT/KR2019/014646 mailed Feb. 21, 2020, 6 pages.

International Preliminary Report on Patentability for International Patent Application No. PCT/KR2019/014646 mailed Apr. 27, 2021, 4 pages.

* cited by examiner

Fig. 5

| | Area% | RT | MW |
|---|---|---|---|
| 1 | 2.05% | 38.67 | >500 |
| 2 | 41.47% | 44.11 | >500 |
| 3 | 1.33% | 76.51 | >500 |
| 4 | 0.01% | 76.55 | >500 |
| 5 | 0.00% | 76.55 | >500 |
| 6 | 8.62% | 81.61 | 474.59 |
| 7 | 30.14% | 84.66 | 449.56 |
| 8 | 1.30% | 103.14 | 297.96 |
| 9 | 5.12% | 106.86 | 267.40 |
| 10 | 2.82% | 110.69 | 236.02 |
| 11 | 2.14% | 116.90 | 185.07 |
| 12 | 0.75% | 127.17 | <100 |
| 13 | 3.54% | 140.57 | <100 |
| 14 | 0.58% | 155.24 | <100 |
| 15 | 0.14% | 181.12 | <100 |

| MW | Area% |
|---|---|
| >500 | 44.9% |
| 100 ~ 500 | 50.1% |
| <100 | 5.0% |

Fig. 7

| | Area% | RT | MW |
|---|---|---|---|
| 1 | 7.07% | 45.65 | >500 |
| 2 | 0.01% | 51.13 | >500 |
| 3 | 22.49% | 55.26 | >500 |
| 4 | 0.04% | 80.89 | 480.49 |
| 5 | 67.37% | 104.74 | 284.85 |
| 6 | 1.26% | 114.73 | 202.84 |
| 7 | 0.44% | 124.42 | 123.34 |
| 8 | 1.31% | 138.39 | <100 |

| MW | Area% |
|---|---|
| >500 | 29.57% |
| 100 ~ 500 | 69.1% |
| <100 | 1.3% |

GRYLLUS BIMACULATUS EXTRACT AND METHOD FOR PREPARING THE SAME

This application is a National Stage Application of PCT/KR2019/014646, filed 31 Oct. 2019, which claims benefit of Patent Application Serial No. 10-2018-0132419, filed 31 Oct. 2018 in Korea and which applications are incorporated herein by reference. To the extent appropriate, a claim of priority is made to each of the above-disclosed applications.

TECHNICAL FIELD

The present application relates to a *Gryllus bimaculatus* extract and a method for preparing the same.

BACKGROUND ART

Since the publication of the UN report recommending insects as food in 2013, as interest in future food and the environment has increased, research on edible insects has been actively conducted. Among edible insects, *Gryllus bimaculatus* belongs to the order Orthoptera, family Gryllidae, and has been registered as a food material in Korea. *Gryllus bimaculatus* is an insect having good nutrients. But, it is unfamiliar to consume *Gryllus bimaculatus* in its original form. In addition, when *Gryllus bimaculatus* was simply dried and powdered as in the prior art, the form of the powder is not fine due to the fat component contained in *Gryllus bimaculatus*, and absorption in the body may be poor.

Accordingly, there have been attempts to utilize useful nutrients of insect food materials, such as *Gryllus bimaculatus*. In particular, as for *Gryllus bimaculatus*, a lot of research has been done on nutritional components. So, there have been attempts to using it as a feed additive for fish farming as described in Korean Patent Unexamined Publication No. 10-2016-0134939 or a functional material as described in Korean Patent No. 10-1702851. However, research for increasing the content of proteins (especially, polypeptides of 500 Da or less) for absorption in the body to increase its utility as a food material has been insufficient, and development as a food material has not been done much.

Prior art Documents (Patent Document 1) Korean Patent Unexamined Publication No. 10-2016-0134939 (24 Nov. 2016)

(Patent Document 2) Korean Patent No. 10-1702851 (31 Jan. 2017)

DISCLOSURE OF THE INVENTION

Technical Problem

The present application is to provide a *Gryllus bimaculatus* extract which is improved to allow nutrients contained in *Gryllus bimaculatus* to be used for human food and a method for preparing the same.

Technical Solution

According to one aspect of the present application, there is provided a method for preparing a *Gryllus bimaculatus* extract, the method comprising: a step for heating *Gryllus bimaculatus* at a temperature of 100° C. or more; and a step for treating a product of the heating with a proteolytic enzyme.

According to another aspect of the present application, there is provided a *Gryllus bimaculatus* extract having a protein content of 40 wt % or more based on the total weight of solids of the *Gryllus bimaculatus* extract, wherein a polypeptide having a size of 500 Da or less and a free amino acid is included in a total content of 60 wt % or more based on the total weight of proteins contained in the *Gryllus bimaculatus* extract.

Advantageous Effects

The *Gryllus bimaculatus* extract according to the present application has high contents of polypeptides having a size of 500 Da or less and free amino acids and thus has excellent absorptivity into the body and is highly useful as a food material and also highly applicable as a food material.

BRIEF DESCRIPTION OF THE DRAWINGS

FIG. 5 is the result table obtained by calculating the content distribution according to the size of polypeptides.

FIG. 7 is the result table obtained by calculating the content distribution according to the size of polypeptides.

MODE FOR CARRYING OUT THE INVENTION

Figure 1:
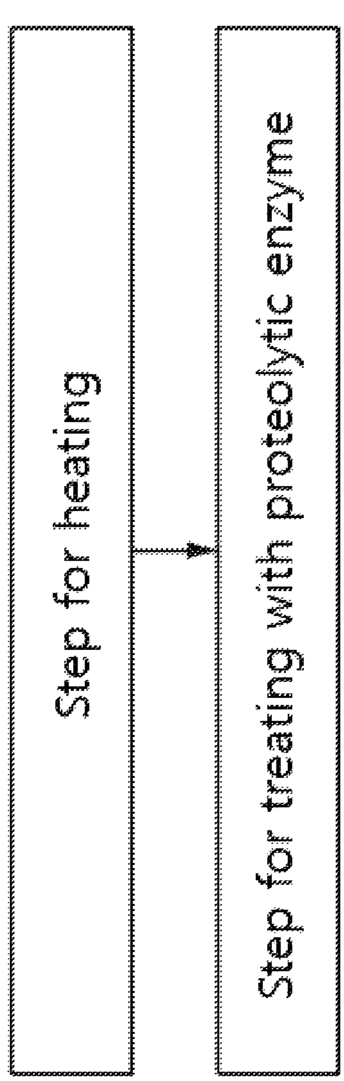
FIG. 1 is a flow chart showing a method for preparing a *Gryllus bimaculatus* extract.

Hereinafter, the present application will be specifically described.

One aspect of the present application provides a method for preparing a *Gryllus bimaculatus* extract.

The method for preparing a *Gryllus bimaculatus* extract of the present application comprises: a step for heating *Gryllus bimaculatus* at a temperature of 100° C. or more; and a step for treating a product of the heating with a proteolytic enzyme.

First, a step for heating *Gryllus bimaculatus* at a temperature of 100° C. or more is performed.

The step for heating *Gryllus bimaculatus* at a temperature of 100° C. or more is a process for: sterilizing the *Gryllus bimaculatus* ; and enhancing the extraction efficiency of proteins which is one of the useful ingredients contained in the *Gryllus bimaculatus*. In addition, the above process plays a role in facilitating the preparation of the *Gryllus bimaculatus* extract.

A heated product of the *Gryllus bimaculatus* means the *Gryllus bimaculatus* heated at a temperature of 100° C. or more. The heated product may be a mixture containing

*Gryllus bimaculatus* raw material and useful ingredients extracted from the *Gryllus bimaculatus* raw material.

Herein, a certain amount of a solvent may be added to further improve the protein extraction efficiency. The content of the solvent may be in a range consisting of one lower limit selected from 100 parts by weight, 150 parts by weight, 200 parts by weight, 250 parts by weight, 300 parts by weight, 350 parts by weight, and 400 parts by weight, and/or one upper limit selected from 3000 parts by weight, 2800 parts by weight, 2600 parts by weight, 2500 parts by weight, 2400 parts by weight, 2200 parts by weight, and 2000 parts by weight, based on a total of 100 parts by weight of the *Gryllus bimaculatus* . For example, it may be 100 to 3000 parts by weight, 100 to 2800 part by weight, 150 to 2600 parts by weight; specifically, 200 to 2500 parts by weight, 250 to 2400 parts by weight, or 300 to 2200 parts by weight; and more specifically, 400 to 2000 parts by weight. When the solvent added concerning a total of 100 parts by weight of the *Gryllus bimaculatus* satisfies the above range, the *Gryllus bimaculatus* extraction efficiency is improved and a solids content is increased so that a process's economic efficiency in a concentration process, etc. is improved, As for the solvent, any solvent that does not degrade the efficiency of extracting the *Gryllus bimaculatus* may be used without limitation. For example, the solvent may be, but is not limited to, water, hexane, ether, etc.

The temperature of heating the *Gryllus bimaculatus* may be in a range consisting of one lower limit selected from 100° C., 102° C., 104° C., 105° C., 106° C., 108° C., 110° C., 112° C., 114° C., 115° C., 116° C., 118° C., 120° C., 122° C., 124° C., 125° C., 126° C., 128° C., 130° C., 132° C., 134° C., 135° C., 136° C., 138° C., and 140° C., and/or one upper limit selected from. 150° C., 149° C., 148° C., 147° C., 146° C., 145° C., 144° C., 143° C., 142° C., 141° C., 140° C., 139° C., 138° C., 137° C., 136° C., 135° C., 134° C., 133° C., 132° C., 131° C., 130° C., 128° C., 126° C. 125° C., 124° C., 122° C., and 120° C. For example, it may be 100° C. to 150° C. inclusive, 105° C. to 145° C. inclusive, 110° C. to 140° C. inclusive, or 100° C. to 130° C. inclusive, and specifically 100° C. to 120° C. inclusive. When the temperature of heating the *Gryllus bimaculatus* satisfies the above range, the efficiency of extracting useful ingredients contained in the *Gryllus bimaculatus* can be improved.

The step for heating the *Gryllus bimaculatus* may be performed under a pressurized condition, as needed. For example, the step for heating the *Gryllus bimaculatus* may be performed under a pressurized condition consisting of one lower limit selected from 1 kg/cm$^2$, 1.1 kg/cm$^2$, 1.2 kg/cm$^2$, 1.3 kg/cm$^2$, and 1.4 kg/cm$^2$, and/or one upper limite selected from 2.0 kg/cm$^2$, 1.9 kg/cm$^2$, 1.8 kg/cm$^2$, 1.7 kg/cm$^2$, 1.6 kg/cm$^2$, and 1.5 kg/cm$^2$. For example, it may be performed under a pressurized condition in a range of 1 to 2 kg/cm$^2$, 1.1 to 1.9 kg/cm$^2$, 1.2 to 1.8 kg/cm$^2$, 1.3 to 1.7 kg/cm$^2$, 1.4 to 1.6 kg/cm$^2$, or 1 to 1.5 kg/cm$^2$.

The time of heating the *Gryllus bimaculatus* may be in a range consisting of one lower limit selected from 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28minutes, 29 minutes, and 30 minutes, and/or one upper limit selected from one upper limit selected from 60 minutes, 59 minutes, 58 minutes, 57 minutes, 56 minutes, 55 minutes, 54 minutes, 53 minutes, 52 minutes, 51 minutes, 50 minutes, 49 minutes, 48 minutes, 47 minutes, 46 minutes, 45 minutes, 44 minutes, 43 minutes, 42 minutes, 41 minutes, 40 minutes, 39 minutes, 38 minutes, 37 minutes, 36 minutes, and 35 minutes. For example, it may be 10 to 60 minutes, 15 to 50 minutes, 15 to 45 minutes, 20 to 35 minutes, or 25 to 30 minutes.

The Brix of the heated product may be in a range consisting of one lower limit selected from 0.3, 0.31, 0.32, 0.33, 0.34, and 0.35, and/or one upper limit selected from 0.5,0.49, 0.48, 0.47, 0.46, 0.45, 0.44, 0.42, 0.41, 0.4, 0.39, 0.38, 0.37, and 0.36. For example, it may be 0.3 to 0.5, 0.31 to 0.45, 0.32 to 0.4, 0.33 to 0.4, or 0.35 to 0.39.

When the heated product satisfies the above Brix range, the Brix of the extract can be increased in a short time (about 10 minutes) upon a later proteolytic enzyme treatment.

The step for treating the heated product with a proteolytic enzyme is a process for degrading proteins which is one of the useful ingredients contained in the *Gryllus bimaculatus* into free amino acids or polypeptides to make forms that are easy to be absorbed into the body.

The proteolytic enzyme is not particularly limited but may be one that is widely used commercially in consideration of economy. Specifically, it may be pepsin, trypsin, Flavourzyme®, Protamex®, papain, alpha chymotrypsin, pancrease, and the like, and more specifically, Flavourzyme®, Protamex®, and the like. Flavourzyme® is a proteolytic enzyme derived from *Aspergillus oryzae* and contains both endoprotease and exoprotease properties. Protamex® is a proteolytic enzyme derived from *Bacillus subtillis* and contains an endoprotease property.

The proteolytic enzyme may be treated in a concentration in a range consisting of one lower limit selected from 0.5 parts by weight, 1 part by weight, 2 parts by weight, 3 parts by weight, 3.33 parts by weight, 4 parts by weight, 5 parts by weight, 5.5 parts by weight, 6 parts by weight, 6.5 parts by weight, 7 parts by weight, 8 parts by weight, 9 parts by weight, and 10 parts by weight, and/or one upper limit selected from 160 parts by weight, 150 parts by weight, 140 parts by weight, 135 parts by weight, 130 parts by weight, 120 parts by weight, 115 parts by weight, 110 parts by weight, 100 parts by weight, 90 parts by weight, 80 parts by weight, 70 parts by weight, 67 parts by weight, 60 parts by weight, 50 parts by weight, and 40 parts by weight, based on a total of 100 parts by weight of solids of the heated product (the pulverized product. when the pulverization step is performed after the heating) of the *Gryllus bimaculatus*. For example, it may be treated in a concentration of 0.5 to 160 parts by weight, 2 to 120 parts by weight, 4 to 90 parts by weight, 5 to 60 parts by weight, or 10 to 45 parts by weight, 15 to 40 parts by weight.

The Brix of the *Gryllus bimaculatus* extract treated with the proteolytic enzyme may be in a range consisting of one lower limit selected from 0.5, 0.55, 0.6, 0.65, 0.7, 0.75, 0.8, 0.85, 0.9, and 0.95, and/or one upper limit selected from 1.5, 1.4, 1.3, 1.2, 1.1, and 1. For example, it may be 0.5 to 1.5, 0.6 to 1.4, 0.7 to 1.3, 0.8 to 1.2, or 0.9 to 1.1.

The proteolytic enzyme treatment time may be in a range consisting of one lower limit selected from 5 minutes, 10 minutes, 20 minutes, 30 minutes, 45 minutes, 1 hour, and/or one upper limit selected from 5 hours, 4 hours, 3.5 hours, 3 hours, 2.5 hours, 2 hours, 1.5 hours. For example, the proteolytic enzyme may be treated for 5 minutes to 5 hours, for 10 minutes to 4 hours, or for 20 minutes to 4 hours, specifically for 30 minutes to 2 hours, and more specifically for 40 minutes to 1.5 hours, When the content and/or treatment time of the proteolytic enzyme satisfy the above ranges, the content of nutrients can be increased.

Meanwhile, the method may further comprise a step for fasting the *Gryllus bimaculatus*, before the step for heating the *Gryllus bimaculatus*.

The step for fasting the *Gryllus bimaculatus* is a process for lowering contents of a feed that remained in a gut of the *Gryllus bimaculatus* and excreta to remove unique off-taste or off-flavor of the *Gryllus bimaculatus* or feeling of irritation. While an appropriate temperature and humidity are maintained, the *Gryllus bimaculatus* is grown. The *Gryllus bimaculatus* is reared mainly on a diet such as sawdust or wheat bran. When the *Gryllus bimaculatus* is processed without fasting, strong off-taste, off-flavor, or feeling or irritation remains due to the residual feed in the gut or the excreta of the *Gryllus bimaculatus* despite the processing. Therefore, through the fasting process, as described above, the off-taste, off-flavor, or feeling of irritation inherent in the *Gryllus bimaculatus* can be reduced.

The fasting step as described above may be performed for a time in a range consisting of one lower limit selected from 1 hour, 2 hours, 3 hours, 5 hours, 7 hours, 9 hours, 10 hours, 12 hours, 15 hours, and 18 hours, and/or one upper limit selected from 72 hours, 65 hours, 60 hours, 54 hours, 48 hours, 42 hours, 36 hours, 30 hours, and 24 hours. For example, it may be performed for 1 hour to 72 hours, specifically for 12 hours to 36 hours, and more specifically for 18 hours to 30 hours. When the fasting time satisfies the above range, the feed in the gut and the excreta of the *Gryllus bimaculatus* are sufficiently removed, and the off-taste, off-flavor, or feeling of irritation is lost.

In addition, the additional inclusion of a step for rearing the *Gryllus bimaculatus* on a grain diet such as wheat flour, etc. instead of the diet such as sawdust or wheat bran, before the fasting step, can further reduce the off-taste, off-flavor, or feeling of irritation of the *Gryllus bimaculatus*.

In addition, the method may further include a step for pulverizing in order to improve the working efficiency of the proteolytic enzyme, after the step of heating the fasted *Gryllus bimaculatus* and before the step of treating the proteolytic enzyme. Herein, as for the pulverization, the fasted and then heated *Gryllus bimaculatus* may be cut or disassembled for each part, and then only the necessary parts may be selectively pulverized, or all parts may be pulverized without a cutting or disintegration process.

In addition, herein, to facilitate the pulverization as described above and improve the acting efficiency of the proteolytic enzyme, a solids content in the pulverized *Gryllus bimaculatus* product may be adjusted by adding a certain amount of a solvent. The pulverized product may mean the *Gryllus bimaculatus* pulverized before the proteolytic enzyme treatment. As for the solvent, any solvent that does not degrade the action of the proteolytic enzyme may be used without limitation. For example, the solvent may be, but is not limited to, water, hexane, ether, etc.

Herein, the pulverized *Gryllus bimaculatus* product may have a solids content in a range consisting of one lower limit selected from 1.25 wt %, 1.5 wt %, 1.75 wt %, 2 wt %, 2.5 wt %, 3 wt %, and 5 wt %, and/or one upper limit selected from 20 wt %, 15 wt %, 10 wt %, and 7 wt %, based on the total weight of the pulverized *Gryllus bimaculatus* product. For example, it may have a solids content of 1.25 to 20 wt %, 1.25 to 15 wt %, 2.5 to 10 wt %, or 5 to 10 wt %.

When adding the solvent to the pulverized *Gryllus bimaculatus* product and thus a solids content in the pulverized *Gryllus bimaculatus* product satisfies the range as described above, the hydrolysis efficiency due to the proteolytic enzyme can be enhanced. When a solids content in the pulverized *Gryllus bimaculatus* product satisfies the above range, the efficiency of a later concentration process is improved to enhance a process's economic efficiency.

Next, a step for powdering a product of the enzyme treatment, to which the proteolytic enzyme was treated, is performed. Namely, the method for preparing a *Gryllus bimaculatus* extract may further include a step for powdering the product of the enzyme treatment.

The step for powdering the product of the enzyme treatment is a process that allows the *Gryllus bimaculatus* product of the enzyme treatment to be easily stored or distributed so as to enhance the applicability as a food material.

The step for powdering the product of the enzyme treatment may be performed through powdering methods generally used in the prior food field. For example, it may be performed by hot-air drying, freeze-drying, or spray drying.

The hot-air drying may be performed at a temperature range consisting of one lower limit selected from 40° C., 45° C., 50° C., 55° C., and 60° C., and/or one upper limit selected from 80° C., 75° C., 70° C., and 65° C. For example, the hot-air drying may be performed at a temperature of 40° C. to 80° C., specifically 50° C. to 70° C. The time of the hot-air drying may be in a range consisting of one lower limit selected from 24 hours, 30 hours, and 36 hours, and/or one upper limit selected from 72 hours, 66 hours, 60 hours, 54 hours, and 48 hours. For example, the hot-air drying may be performed at a condition where hot air is provided for 24 hours to 72 hours, specifically 30 hours to 60 hours.

The freeze-drying may be performed at a temperature range consisting of one lower limit selected from −70° C., −65° C., −60° C., −55° C., and −50° C., and/or one upper limit selected from 30° C., 25° C., 20° C., 15° C., 10° C., 5° C., and 0° C. For example, the freeze-drying may be performed at a temperature of −70° C. to 30° C., specifically −50° C. to 0° C. The time of the freeze-drying may be in a range consisting of one lower limit selected from 3 hours, 4 hours, 5 hours, and 6 hours, and/or one upper limit selected from 60 hours, 48 hours, 42 hours, 36 hours, 30 hours, 24 hours, 18 hours, and 12 hours. For example, the freeze-drying may be performed at a condition where cooling is provided for 3 hours to 60 hours, specifically 6 hours to 24 hours. In addition, the freeze-drying may be set by combining the above temperature range stage by stage.

Additionally, a process of secondary drying at a temperature of 10° C. to 40° C., specifically 20° C. to 30° C. for 3 hours to 24 hours, specifically 6 hours to 12 hours may be performed to remove residual water.

In addition, the spray drying may be performed at an inlet temperature range consisting of one lower limit selected from 100° C., 110° C., 120° C., and 130° C., and/or one upper limit selected from 150° C., 140° C., and 130° C. For example, the spray drying may be performed at an inlet temperature of 100° C. to 150° C., specifically 110° C. to 140° C. The spray drying may be performed at an outlet temperature range consisting of one lower limit selected from 50° C., 55° C., 60° C., 65° C., and 70° C., and/or one upper limit selected from 100° C., 95° C., 90° C., 85° C., 80° C., 75° C., and 70° C. For example, the spray drying may be performed at an outlet temperature condition of 50° C. to 100° C., specifically 60° C. to 90° C.

Meanwhile, before the powdering, the product of the enzyme treatment may be further passed through at least one step selected from a step for heating and cooling, a step for filtering, and a step for concentrating.

The step for heating and cooling the product of the enzyme treatment is a process for inactivating the proteolytic enzyme in the product of the enzyme treatment, as well as sterilizing microorganisms to improve the safety as a food. The heating step may be performed at a temperature range consisting of one lower limit selected from 90° C., 95° C., 100° C., 105° C., and 110° C., and/or one upper limit selected from 150° C., 145° C., 140° C., 135° C., 130° C., 125° C., 120° C., 115° C., and 110° C. For example, the heating step may be performed at a temperature condition of 90° C. to 150° C., specifically 95° C. to 130° C., and more specifically 100° C. to 120° C.

The time of heating may be in a range consisting of one lower limit selected from 5 minutes, 6 minutes, 7 minutes, 8 minutes, 9 minutes, and 10 minutes, and/or one upper limit selected from 120 minutes, 100 minutes, 80 minutes, 60 minutes, 40 minutes, 30 minutes, and 20 minutes. For example, the heating step may be performed for a time of 5 minutes to 120 minutes, 6 minutes to 100 minutes, minutes to 80 minutes 8 minutes to 60 minutes 9 minutes to 40 minutes, 10 minutes to 20 minutes. When the temperature and time conditions of the heating step satisfy the above ranges, the inactivation of the proteolytic enzyme or the sterilization of microorganisms can be sufficiently carried out, and destruction of nutrients can be minimized.

In addition, a step for cooling may be performed after the heating step as described above. The cooling step may be performed at a temperature condition consisting of one lower limit selected from 0° C., 1° C., 2° C., 3° C., 4° C., and 5° C., and/or one upper limit selected from 10° C., 9° C., 8° C., 7° C., 6° C., and 5° C. For example, the cooling step may be performed at a temperature condition of 0° C. to 10° C., specifically 1° C. to 7° C., and more specifically 3° C. to 5° C. The time of the cooling step may be in a range consisting of one lower limit selected from 30 minutes, 35 minutes, 40 minutes 45 minutes, 50 minutes, 55 minutes, and 60 minutes, and/or one upper limit selected from 120 minutes, 110 minutes, 100 minutes, 90 minutes, 80 minutes, and 70 minutes. For example, the cooling step may be performed for a time of 30 minutes to 120 minutes, specifically 45 minutes to 90 minutes, and more specifically 50 minutes to 70 minutes. When the temperature and time conditions of the cooling step satisfy the above ranges, the product of the enzyme treatment can be sufficiently cooled, and a process's economic efficiency cannot deteriorate.

In addition, the step for filtering the product of the enzyme treatment is a process for reducing the feeling of irritation derived from the *Gryllus bimaculatus*, as well as further improving the efficiency of the powdering as described above. In the step for filtering the product of the enzyme treatment, a precipitate is precluded, and a water-soluble supernatant is separated from the product of the enzyme treatment. Conventional filtration methods, such as a filter, etc., can be used. For example, the product of the enzyme treatment may be filtered through a filter of 0.2 μm to 5 μm. When the filtration condition as described above is satisfied, the product of the enzyme treatment can be sufficiently separated, and a process's economic efficiency can be improved.

In addition, the step for concentrating the product of the enzyme treatment is a process for increasing a solids content to further improve the usefulness as a food material and may be performed through concentration methods generally used in the prior food field. For example, the concentration may be performed at conditions of 40° C. to 60° C., 10 rpm to 100 rpm, and 20 mbar to 100 mbar using a conventional concentrator. The concentration step may be performed so that the product of the enzyme treatment has a concentration of 5 Brix to 40 Brix, specifically 10 Brix to 30 Brix. Meanwhile, where both the heating and cooling step and the concentration step are performed, only the proteolytic enzyme of the product of the enzyme treatment is briefly inactivated at a temperature or 90° C. or more for 10 minutes or longer, and then the concentration step may be first performed, and the heating and cooling step may be performed after the concentration step.

Another aspect of the present application provides a *Gryllus bimaculatus* extract.

The *Gryllus bimaculatus* extract may be, but not limited to, in the form of a liquid, a gel, or a powder.

The *Gryllus bimaculatus* extract may be one prepared by the method for preparing a *Gryllus bimaculatus* extract as described above.

The *Gryllus bimaculatus* extract may have a protein content in a range consisting of one lower limit selected from 40 wt % or more, 45 wt % or more, 46 wt % or more, 47 wt % or more, 50 wt % or more, 55 wt % or more, 60 wt % or more, 65 wt % or more, 70 wt % or more, and 75 wt % or more, and/or one upper limit selected from 100 wt % or less, 99 wt % or less, 9.5 wt % or less, 90 wt % or less, 85 wt % or less, 80 wt % or less, 75 wt % or less, and 70 wt % or less, based on the total weight of solids of the *Gryllus bimaculatus* extract. For example, it may have a protein content of 40 wt % to 100 wt % inclusive, specifically 40 wt % to 99 wt % inclusive, 40 wt % to 95 wt % inductive, 40 wt % to 90 wt % inclusive, 40 wt % to 80 wt % inclusive, or specifically 45 wt % to 100 wt % inclusive, 45 wt % to 99 wt % inclusive, 45 wt % to 95 wt % inclusive, 45 wt % to 90 wt % inclusive, 45 wt % to 80 wt % inclusive, or 46 wt % to 100 wt % inclusive, 46 wt % to 99 wt % inclusive, 46 wt % to 95 wt % inclusive, 46 wt % to 90 wt % inclusive, 46 wt % to 80 wt % inclusive, or specifically 47 wt % to 100 wt % inclusive, 47 wt % to 99 wt % inclusive, 47 wt % to 95 wt % inclusive, 47 wt % to 90 wt % inclusive, 47 wt % to 80 wt % inclusive.

In addition, the proteins contained in the *Gryllus bimaculatus* extract may include a polypeptide having a size of 500 Da or less and a free amino acid in a total content in a range consisting of one lower limit selected from 60 wt % or more, 65 wt % or more, 69 wt % or more, 70 wt % or more, 75 wt % or more, 80 wt % or more, 85 wt % or more, 90 wt % or more, and 95 wt % or more, and/or one upper limit selected from 100 wt % or less, 99 wt % or less, 98 wt % or less, and 97 wt % or less, of 100 wt % of the total weight of the proteins. For example, the polypeptide having a size of 500 Da or less and the free amino acid may be included in a content of 60 wt % to 100 wt % inclusive, specifically 60 wt % to 99 wt % inclusive, or specifically 65 wt % to 100 wt % inclusive, 65 wt % to 99 wt % inclusive, or specifically 69 wt % to 100 wt % inclusive, 69 wt % to 99 wt % inclusive, or specifically 70 wt % to 100 wt % inclusive, 70 wt % to 99 wt % inclusive.

The polypeptide having a size of 500 Da or less may include a dipeptide or a tripeptide, having a size of 500 Da or less.

The amino acid may mean an amino acid that exists as a single molecule, in contrast to bound amino acids, such as proteins or peptides.

The *Gryllus bimaculatus* extract may include free amino acids in a content in a range consisting of one lower limit selected from 4.5 wt % or more, 4.6 wt % or more, 4.7 wt % or more, 4.8 wt % or more, 4.9 wt % or more, 5 wt % or more, 5.5 wt % or more, 6 wt % or more, 7 wt % or more, 8 wt % or more, 9 wt % or more, and 10 wt % or more, and/or one upper limit selected from 75 wt % or less, 70 wt % or less, 65 wt % or less, 60 wt % or less, and 50 wt % or less, based on the total weight of solids of the *Gryllus bimaculatus* extract. For example, the *Gryllus bimaculatus* extract may include free amino acids in a content of 4.5 wt % to 75 wt % specifically 4.5 wt % to 70 wt % inclusive, 4.5 wt % to 65 wt % inclusive, or specifically 4.7 wt % to 75 wt % inclusive, 4.7 wt % to 70 wt % inclusive, 4.7 wt % to 65 wt % inclusive, or specifically 4.9 wt % to 75 wt % inclusive, 4.9 wt % to 70 wt % inclusive, 4.9 wt % to 65 wt % inclusive. Consequently, the *Gryllus bimaculatus* extract has the advantage of having improved absorptivity into the body.

The *Gryllus bimaculatus* extract may include essential amino acids in a content in a range consisting of one lower limit selected from 30 wt % or more, 31 wt % or more, 32 wt % or more, 33 wt % or more, 34 wt % or more, and 35 wt % or more, and/or one upper limit selected from. 50 wt % or less, 49 wt % or less, 48 wt % or less, 47 wt % or less, 46 wt % or less, 45 wt % or less, 44 wt % or less, 43 wt % or less, 42 wt % or less, 41 wt % or less, and 40 wt % or less, based on the total weight of solids of the *Gryllus bimaculatus* extract. For example, the *Gryllus bimaculatus* extract may include essential amino acids in a content of 30 to 50 wt %, 31 to 49 wt %, 32 to 48 wt %, 33 to 47 wt %, 34 to 46 wt %, 35 to 45 wt %, or 35 to 40 wt %.

The essential amino acids may include histidine, threonine, valine, methionine, phenylalanine, isoleucine, leucine, lysine, or tryptophan, or the like.

In addition, the essential amino acids may be included in any form, such as free amino acids or polypeptides, or the like.

Herein, the essential amino acids may be included in a content in a range consisting of one lower limit selected from 70 wt %, 71 wt %, 71.8 wt %, 72 wt %, 73 wt %, 74 wt %, 74.3 wt %, 75 wt %, 76 wt %, and 76.7 wt %, and/or one upper limit selected from 90 wt %, 89 wt %, 88 wt %, 87 wt %, 86 wt %, 85 wt %, 84 wt %, 83 wt %, 82 wt %, 81 wt %, 80 wt %, 79 wt %, 77 wt %, 76 wt %, and 75 wt %, based on the total weight of proteins contained in the *Gryllus bimaculatus* extract. For example, the essential amino acid may be included in a content of 70 to 90 wt %, 71 to 85 wt %, 71.8 to 80 wt %, or 74 to 90 wt %, 74.3 to 80 wt %, 또는 76 to 90 wt %, 76.7 to 80 wt %.

Another aspect of the present application provides a food comprising the *Gryllus bimaculatus* extract.

The *Gryllus bimaculatus* extract is as described above. In addition, the *Gryllus bimaculatus* extract may be used or included as an ingredient in a composition for a food material or a food.

Hereinafter, the present application will be described in detail through Examples.

However, the following Examples specifically illustrate the present application, and the contents of the present application are not limited by the following Examples.

PREPARATION EXAMPLE 1-1

(1) The Step for Fasting *Gryllus bimaculatus*

40 to 45-day-old *Gryllus bimaculatus* reared on a wheat bran diet was fasted for 24 hours and allowed to release excrement. Then, the *Gryllus bimaculatus* was washed and kept frozen.

(2) The Step for Heating the *Gryllus bimaculatus*

The fasted *Gryllus bimaculatus* was washed. Then, to a total of 100 parts by weight of the *Gryllus bimaculatus,* 1900 parts by weight of water were added and heated at 100° C. for 30 minutes.

(3) The Step for Pulverizing the *Gryllus bimaculatus*

The heated *Gryllus bimaculatus* was pulverized using a homogenizer at 6000 rpm for 10 minutes to make a liquid.

(4) The Step for Treating the *Gryllus bimaculatus* with a Proteolytic Enzyme

Water was added so that the pulverized liquid product had a solids content of 5 wt %. 0.1 parts by weight of Protamex® (Novozymes), which is a proteolytic enzyme, were added to a total of 100 parts by weight of the pulverized *Gryllus bimaculatus* product to react at the temperature of 60° C. for 1 hour, and then the proteolytic enzyme was inactivated at the temperature of 100° C. for 10 minutes.

(5) The Step for Filtering a Product of the Enzyme Treatment

The product of the enzyme treatment was passed through a 1 μm glass fiber filter under reduced pressure to obtain a filtrate.

(6) The Step for Concentrating a Filtrate

The filtrate was concentrated using a reduced pressure concentrator to prepare a concentrate of 10 Brix or more.

(7) The Step for Powdering a Concentrate

The concentrate was powdered through hot-air drying using FISHER ISOTEMP OVEN 300SERIES MODEL 350G at the temperature of 60° C. for 48 hours.

PREPARATION EXAMPLE 1-2

The *Gryllus bimaculatus* extract was prepared in the same way as Preparation Example 1-1, except that (2) the step for heating the *Gryllus bimaculatus* in Preparation Example 1-1 was performed at 60° C. instead of 100° C.

PREPARATION EXAMPLE 1-3

The *Gryllus bimaculatus* extract was prepared in the same way as Preparation Example 1-1, except that (2) the step for heating the *Gryllus bimaculatus* in Preparation Example 1-1 was performed at 80° C instead of 100° C.

PREPARATION EXAMPLE 1-4

The *Gryllus bimaculatus* extract was prepared in the same way as Preparation Example 1-1, except that (2) the step for heating the *Gryllus bimaculatus* in Preparation Example 1-1 was performed at 120° C. instead of 100° C.

PREPARATION EXAMPLE 2-1

The *Gryllus bimaculatus* extract was prepared in the same way as Preparation Example 1-1, except that water was added so that the pulverized *Gryllus bimaculatus* product had a solids content of 1.25 wt % instead of 5 wt % in (4) the step of the proteolytic enzyme treatment in Preparation Example 1-1.

PREPARATION EXAMPLE 2-2

The *Gryllus bimaculatus* extract was prepared in the same way as Preparation Example 1-1, except that water was added so that the pulverized *Gryllus bimaculatus* product had a solids content of 2.5 wt % instead of 5 wt % in (4) the step of the proteolytic enzyme treatment in Preparation Example 1-1.

PREPARATION EXAMPLE 2-3

The *Gryllus bimaculatus* extract was prepared in the same way as Preparation Example 1-1, except that water was added so that the pulverized *Gryllus bimaculatus* product had a solids content of 10 wt % instead of 5 wt % in (4) the step of the proteolytic enzyme treatment in Preparation Example 1-1.

PREPARATION EXAMPLE 2-4

The *Gryllus bimaculatus* extract was prepared in the same way as Preparation Example 1-1, except that water was added so that the pulverized *Gryllus bimaculatus* product had a solids content of 20 wt % instead of 5 wt % in (4) the step of the proteolytic enzyme treatment in Preparation Example 1-1.

PREPARATION EXAMPLE 3-1

The *Gryllus bimaculatus* extract was prepared in the same way as Preparation Example 1-1, except that 0.5 parts by weight, instead of 0.1 parts by weight, of Protamex® (Novozymes), which is a proteolytic enzyme, were added, based on 100 parts by weight of the pulverized *Gryllus bimaculatus* product in (4) the step of the proteolytic enzyme treatment in Preparation Example 1-1.

PREPARATION EXAMPLE 3-2

The *Gryllus bimaculatus* extract was prepared in the same way as Preparation Example 1-1, except that 1 part by weight, instead of 0.1 parts by weight, of Protamex® (Novozymes), which is a proteolytic enzyme, were added, based on 100 parts by weight of the pulverized *Gryllus bimaculatus* product in (4) the step of the proteolytic enzyme treatment in Preparation Example 1-1.

PREPARATION EXAMPLE 3-3

The *Gryllus bimaculatus* extract was prepared in the same way as Preparation Example 1-1, except that 1.5 parts by weight, instead of 0.1 parts by weight, of Protamex® (Novozymes), which is a proteolytic enzyme, were added, based on 100 parts by weight of the pulverized *Gryllus bimaculatus* product in (4) the step of the proteolytic enzyme treatment in Preparation Example 1-1.

PREPARATION EXAMPLE 3-4

The *Gryllus bimaculatus* extract was prepared in the same way as Preparation Example 1-1, except that 2 parts by weight, instead of 0.1 parts by weight, of Protamex® (Novozymes), which is a proteolytic enzyme, were added, based on 100 parts by weight of the pulverized *Gryllus bimaculatus* product in (4) the step of the proteolytic enzyme treatment in Preparation Example 1-1.

PREPARATION EXAMPLE 4-1

The *Gryllus bimaculatus* extract was prepared in the same way as Preparation Example 1-1, except that the concentrate was dried through, instead of hot-air drying, spray drying using LabPlant SD-Basic at the inlet temperature of 130° C. and the outlet temperature of 80° C., and powdered, in (7) the step for powdering the concentrate in Preparation Example 1-1.

PREPARATION EXAMPLE 4-2

The *Gryllus bimaculatus* extract was prepared in the same way as Preparation Example 1-1, except that the concentrate was dried through, instead of hot-air drying, freeze-drying using Heto PowerDry PL9000 under the pressure of 0.09 hPa for 6 hours at −45° C., for 21 hours at −20° C., for 11 hours at −15° C., for 11 hours at −5° C., and for 10 hours at 0° C., followed by secondary drying for 8 hours at 25° C. to dry ail the residual water, and then powdered, in (7) the step for powdering the concentrate in Preparation Example 1-1.

EXPERIMENTAL EXAMPLE 1

The Extraction Efficiency of *Gryllus bimaculatus* Extract Depending on the Heating Temperature When Preparing *Gryllus bimaculatus* Extract The concentration (Brix) of the heated product due to controlling the temperature in the step for heating the *Gryllus bimaculatus* was measured to determine the efficiency of extracting useful ingredients from the *Gryllus bimaculatus*.

The result of measuring the concentration of the heated product obtained by heating at each of the temperature conditions of 60° C., 80° C., 100° C., and 120° C. for 30 minutes, as in Preparation Examples 1-1 to 1-4, was shown in Table 1.

TABLE 1

| Heating temperature (° C.) | Heating time (minutes) | Heated product concentration (Brix) |
|---|---|---|
| Preparation Example 1-2) 60 | 30 | 0.07 |
| Preparation Example 1-3) 80 | 30 | 0.08 |
| Preparation Example 1-1) 100 | 30 | 0.33 |
| Preparation Example 1-4) 120 | 30 | 0.35 |

As shown in Table 1, the result showed that the concentration of the heated product when heating at a temperature of 100° C. or more was at least about 4 times higher than that when heating at a temperature of less than 100° C. Thus, it was found that the efficiency of extracting proteins which is a useful ingredient contained in the *Gryllus bimaculatus* was improved.

After heating at the temperature conditions of 100° C. and 120° C., at which the concentration of the heated product was high as described above, the heated product was pulverized and then treated with the proteolytic enzyme. The result of measuring the extraction efficiency of the product of the enzyme treatment depending on the enzyme treatment time was shown in Table 2. As for a control group, after heating at the condition of 100° C. and pulverization, the proteolytic enzyme was not treated (Unit of the concentration of the product of the enzyme treatment depending on the enzyme treatment time: Brix).

TABLE 2

| Heating temperature (° C.) | Heating time (minutes) | Heated product concentration (Briz) | Enzyme treatment Protamex ® | Enzyme treatment time (minutes) 0 | 10 | 20 | 30 | 40 | 50 | 60 |
|---|---|---|---|---|---|---|---|---|---|---|
| Preparation Example 1-1) 100 | 30 | 0.33 | ○ | 0.43 | 0.83 | 0.83 | 0.88 | 0.93 | 0.96 | 0.98 |
| Preparation Example 1-4) 120 | 30 | 0.35 | ○ | 0.43 | 0.8 | 0.83 | 0.87 | 0.92 | 0.97 | 0.98 |
| 100 (No enzyme treatment was performed in Preparation Example 1-1) | 30 | 0.33 | X | 0.43 | 0.42 | 0.44 | 0.44 | 0.44 | 0.45 | 0.46 |

As shown in Table 2, the result showed that the extract concentration (Brix) when first heating the *Gryllus bimaculatus* at a temperature of 100° C. or more and then treating the *Gryllus bimaculatus* with the proteolytic enzyme was increased about two times that directly after the enzyme treatment for 10 minutes or less.

EXPERIMENTAL EXAMPLE 2

Analysis of Nutrients in *Gryllus bimaculatus* Biological Raw Material and *Gryllus bimaculatus* Extract Powder The nutrient contents in: the *Gryllus bimaculatus* biological raw material, which was obtained by fasting the 40 to 45-day-old *Gryllus bimaculatus* reared on a wheat bran diet for 24 hours, allowing the same to release excrement, and then keeping the same frozen; commercially available *Gryllus bimaculatus* powder (MG natural); and the *Gryllus bimaculatus* extract powder prepared in Preparation Example 1-1, were analyzed according to Korean food code. The result was shown in Table 3 below.

It was found that the *Gryllus bimaculatus* extract powder prepared in Preparation Example 1-1 had a lower fat content but a higher protein content than the *Gryllus bimaculatus* biological raw material or the commercially available *Gryllus bimaculatus* powder.

TABLE 3

| Test item | Unit | Test method | Gryllus bimaculatus biological raw material | Commercially available Gryllus bimaculatus powder | Gryllus bimaculatus extract powder of Preparation Example 1-1 |
|---|---|---|---|---|---|
| Calorie | kcal/100 g | Korean food code | 156 | 455 | 310 |
| Carbo-hydrates | g/100 g | Korean food code | 2.45 | 3.82 | 1.13 |
| Proteins | g/100 g | Korean food code, Protein Analyzer | 20.2 | 68.2 | 76.4 |
| Fats | g/100 g | Korean food code | 7.73 | 19.2 | 0.16 |
| Sugars | g/100 g | Korean food code, HPLC/RI | — | 0.673 | — |
| Saturated fats | g/100 g | Korean food code, GC/FID | 2.7 | 5.86 | 0.05 |
| Trans fats | g/100 g | Korean food code, GC/FID | 0.077 | 0.213 | 0 |
| Cholesterols | mg/100 g | Korean food code, GC/FID | 115 | 562 | 11.7 |
| Sodium | mg/100 g | Korean food code, ICP/OES | 139 | 478 | 536 |
| Water | g/100 g | Korean food code | 68.1 | 2.3 | 2.3 |
| Ashes | g/100 g | Korean food code | 1.52 | 6.48 | 19.97 |
| Dietary fibers | g/100 g | Korean food code | 2.16 | 2.87 | 0.78 |

(In the above table, "—" means a value below the detection limit.)

EXPERIMENTAL EXAMPLE 3

The Content of L-tyrosine in the *Gryllus bimaculatus* Extract Depending on the Concentration of the Proteolytic Enzyme Added During the Preparation of the *Gryllus bimaculatus* Extract To determine the appropriate enzyme concentration required for protein hydrolysis through proteolytic enzyme treatment of the *Gryllus bimaculatus*, an L-tyrosine content in the extract prepared by varying the treatment concentration of the proteolytic enzyme was measured to determine the degree of hydrolysis.

As in Preparation Example 1-1, and Preparation Examples 3-1 to 3-4, Protamex® (Novozymes) was added to the pulverized, liquid *Gryllus bimaculatus* product, in concentrations of 0.1 parts by weight, 0.5 parts by weight, 1.0 part by weight, 3.5 parts by weight, and 2.0 parts by weight, based on a total of 100 parts by weight of the pulverized, liquid *Gryllus bimaculatus* product, to react, at the temperature of 60° C. for 1 hour. The proteolytic enzyme was inactivated at the temperature of 100° C. for 10 minutes, and then the contents of L-tyrosine in the prepared extracts were measured.

Figure 2:
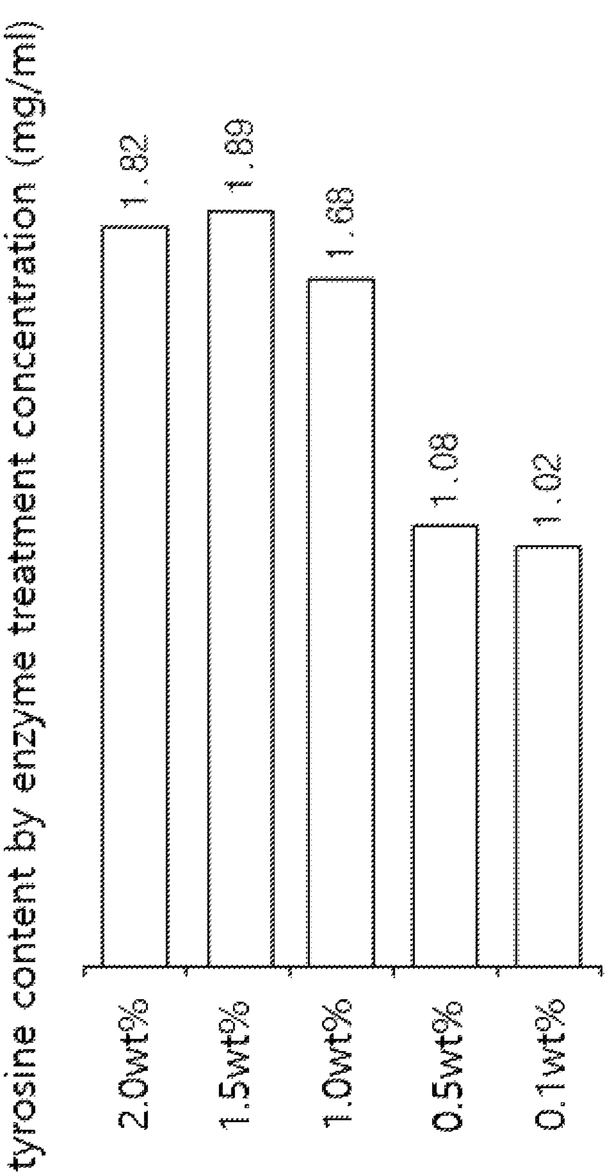
FIG. 2 is a graph showing the result of measuring the content of L-tyrosine in the extract according to the concentration of the proteolytic enzyme added during the preparation of the *Gryllus bimaculatus* extract of the present application.

As shown in FIG. 2, the result showed that the hydrolysis efficiency improved as the treatment concentration of the Protamex® enzyme increased. Given economic feasibility, it was judged that a sufficient hydrolysis effect could be achieved by treatment with only a concentration of 0.1 wt % of the proteolytic enzyme, based on the total weight of the pulverized *Gryllus bimaculatus* product.

EXPERIMENTAL EXAMPLE 4

The Content of L-tyrosine in the *Gryllus bimaculatus* Extract Depending on the Content of the Pulverized *Gryllus bimaculatus* Product During the Preparation of the *Gryllus bimaculatus* Extract To determine the appropriate solids content required for protein hydrolysis through proteolytic enzyme treatment of the *Gryllus bimaculatus*, an L-tyrosine content in the extract prepared by varying the solids content of the pulverized, liquid *Gryllus bimaculatus* product was measured to determine the degree of hydrolysis.

As in Preparation Example 1-1, and Preparation Examples 2-1 to 2-4, after making the solids contents in the pulverized *Gryllus bimaculatus* products be 5 wt %, 1.25 wt %, 2.5 wt %, 10 wt %, and 20 wt %, respectively, the contents of L-tyrosine in the prepared extracts were measured.

Figure 3:
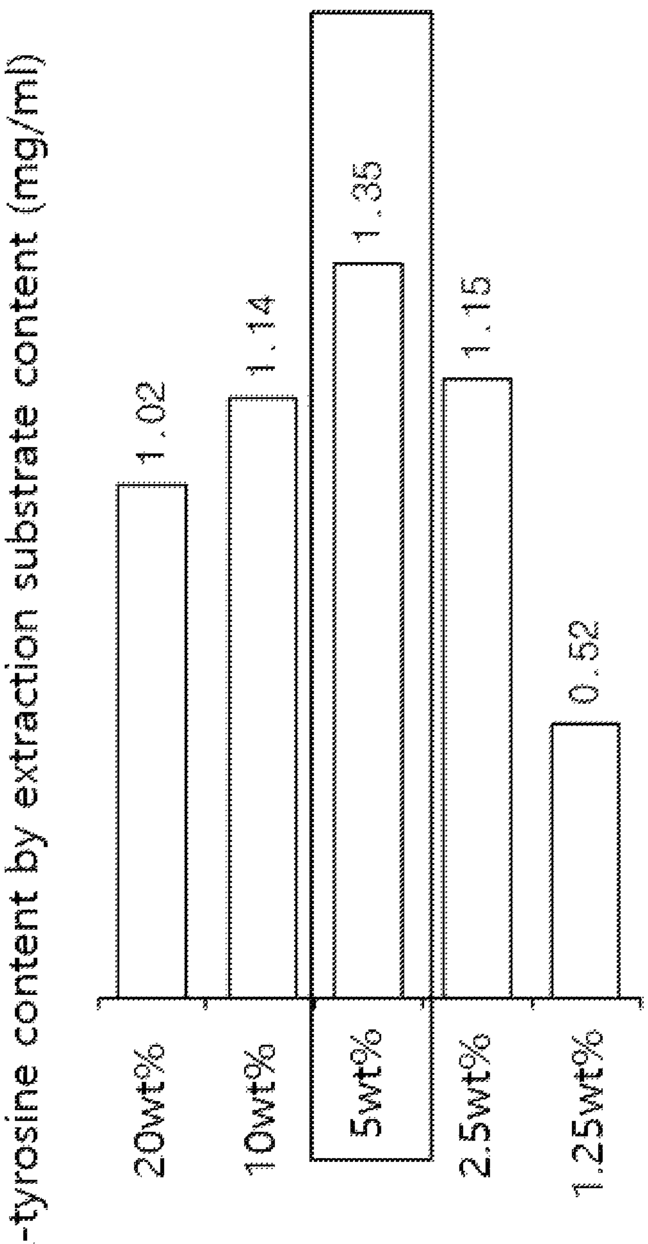
FIG. 3 is a graph showing the result of measuring the content of L-tyrosine in the extract according to the content of the pulverized *Gryllus bimaculatus* product during the preparation of the *Gryllus bimaculatus* extract of the present application.
Figure 4:
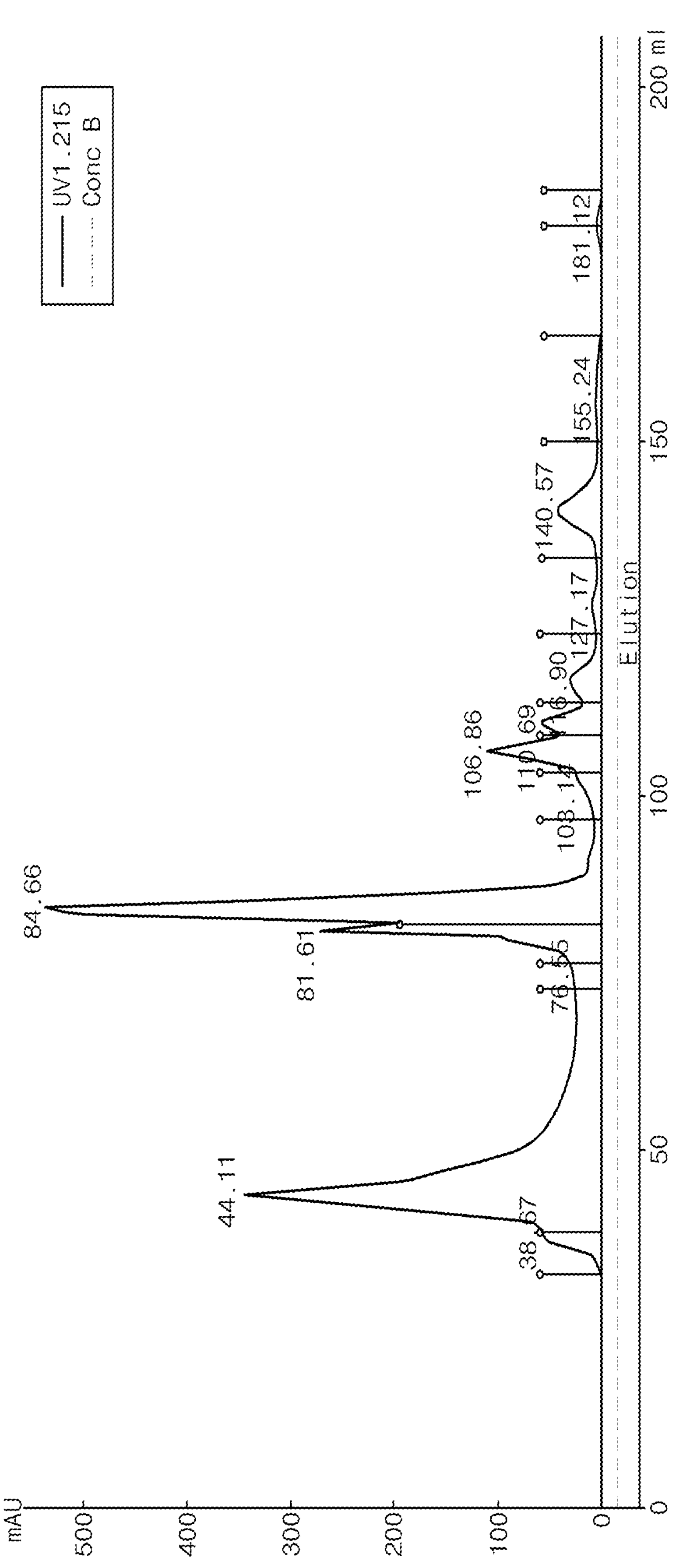
FIG. 4 is a graph showing the result of Fast Protein Liquid Chromatography (FPLC) analysis of proteins in the pulverized *Gryllus bimaculatus* product before the proteolytic enzyme treatment.

As shown in FIG. 3, the result showed that the hydrolysis efficiency was high when the solids content in the pulverized *Gryllus bimaculatus* product was 5 wt %.

EXPERIMENTAL EXAMPLE 5

Analysis of Protein Composition in the *Gryllus bimaculatus* Extract

The total of 100 parts by weight of the pulverized, liquid *Gryllus bimaculatus* product having the solids content of 5 wt % prepared in Preparation Example 1-1 were treated with 0.1 parts by weight of the Protamex® enzyme for 1 hour to react. The proteolytic enzyme was inactivated at the temperature of 100° C. for 10 minutes. Then the prepared extract was filtered through a 0.2 μm glass fiber filter paper under reduced pressure to obtain a filtrate. The degree of proteolysis was analyzed by Fast Protein Liquid Chromatography (FPLC).

As for a control group, the pulverized product before treatment of the Protamex enzyme as described above was diluted with water to have the solids content, of 5 wt %. Then, the dilute was analyzed by FPLC. Herein, for FPLC, 100% water was used as a solvent, Hiload 16/600 superdex 30 pg was used as a column, the fraction size was set to be 1 mL, and the flow rate was set to be 1 mL/min.

Figure 6:
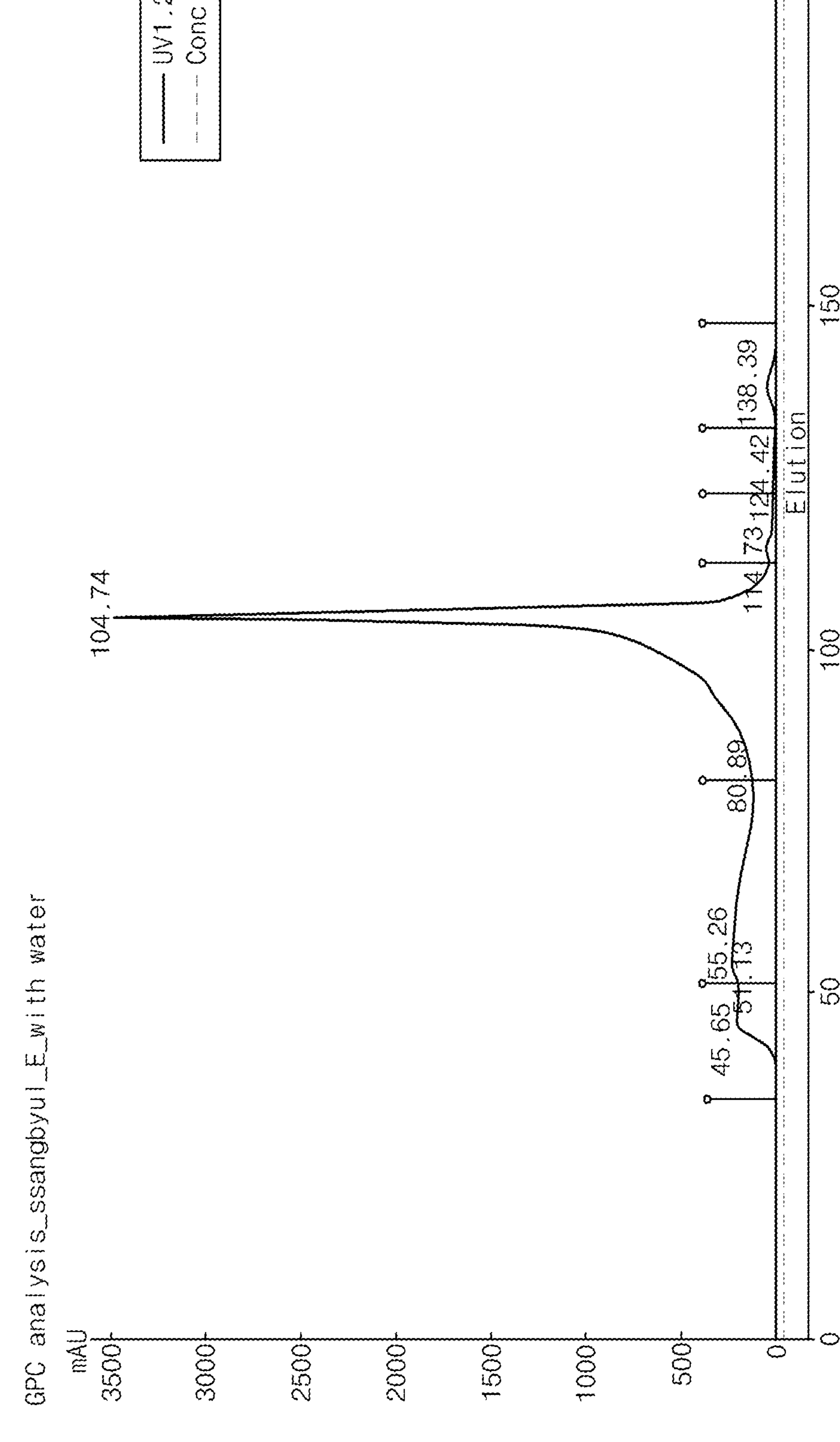
FIG. 6 is a graph showing the result of Fast Protein Liquid Chromatography (FPLC) analysis of proteins in the *Gryllus bimaculatus* extract treated with the proteolytic enzyme.

According to FIGS. 4 to 7, the result showed that the pulverized product before the proteolytic enzyme treatment had the contents of polypeptides having a size of 500 Da or less (after 78.51 mL) and free amino acids of 55.1 wt % based on the total weight of the proteins (FIGS. 4 and 5), while the extract after the proteolytic enzyme treatment had the contents of polypeptides having a size of 500 Da or less (after 78.51 mL) and free amino acids of 70.4 wt % based on the total weight of the proteins (FIGS. 6 and 7). In addition, it was found that the pulverized product having 0.37 Brix before the proteolytic enzyme treatment had 1.8 Brix after the proteolytic enzyme treatment, indicating that the concentration increased.

Given that the average size of amino acids is about 138 Da, it was found that in the *Gryllus bimaculatus* extract prepared through the proteolytic enzyme treatment, small polypeptides having a size equal to or smaller than tripeptides and being able to be absorbed directly into the small intestine formed the majority.

EXPERIMENTAL EXAMPLE 6

Analysis of Protein Composition in the *Gryllus bimaculatus* Extract Powder

The contents of water-soluble proteins in the *Gryllus bimaculatus* extract powders prepared in Preparation Examples 1-1, 4-1, and 4-2 were analyzed by gas chromatography and shown in Table 4 below.

The result showed that the *Gryllus bimaculatus* biological raw material contained 20.2 wt % of the proteins, while the *Gryllus bimaculatus* extract powders of the present application had the protein contents of 45 wt % or more, among which, essential amino acids (histidine, threonine, valine, methionine, phenylalanine, isoleucine, leucine, lysine, and tryptophan) were 30 wt % or more. In addition, it was found that the *Gryllus bimaculatus* extract powders had the content of free amino acids of 4.5 wt % or more.

TABLE 4

| Powdering method | Total proteins (wt %) | Essential amino acids (wt %) | Free amino acids (wt %) |
|---|---|---|---|
| Preparation Example 1-1) Hot-air drying | 50.053 | 35.97 | 4.953 |
| Preparation Example 4-1) Spray-drying | 46.317 | 35.56 | 4.934 |
| Preparation Example 4-2) Freeze-drying | 47.713 | 35.49 | 5.132 |

The invention claimed is:

1. A method for preparing a *Gryllus bimaculatus* extract, the method comprising:

adding a solvent and heating a *Gryllus bimaculatus* in the solvent at a temperature of 100° C. or more, wherein the solvent comprises at least one selected from the group consisting of water, hexane, and ether, wherein the heating time is 25 to 30 minutes;

pulverizing a heated product of *Gryllus bimaculatus* after the heating; and treating a pulverized product of *Gryllus bimaculatus* obtained by the pulverizing with a proteolytic enzyme, to obtain a *Gryllus bimaculatus* extract wherein the proteolytic enzyme includes Protamex®, and a solid content of the pulverized product of *Gryllus bimaculatus* is 3 to 7 wt % based on the total weight of the pulverized product of *Gryllus bimaculatus*, wherein the proteolytic enzyme is present in a concentration of 1 to 2 parts by weight, with respect to a total of 100 parts by weight of the pulverized product of *Gryllus bimaculatus*, and the pulverized product *Gryllus bimaculatus* is treated with the proteolytic enzyme for 10 minutes to 1 hours, and wherein the *Gryllus bimaculatus* extract comprises L-tyrosine in an amount of 1.68 mg/ml or more.

2. The method for preparing the *Gryllus bimaculatus* extract of claim 1, further comprising powdering a product of the enzyme treatment.

3. The method for preparing the *Gryllus bimaculatus*extract of claim 2, wherein the powdering a product of the enzyme treatment includes at least one selected from among hot-air drying, freeze-drying, and spray-drying, of the product of the enzyme treatment.

4. The method for preparing the *Gryllus bimaculatus* extract of claim 1, further comprising filtering or concentrating the product of the enzyme treatment after the enzyme treatment.

5. The method for preparing the *Gryllus bimaculatus* extract of claim 1, wherein the method comprising fasting the *Gryllus bimaculatus*.

6. The method for preparing the *Gryllus bimaculatus* extract of claim 1, wherein the solid content of the pulverized product of *Gryllus bimaculatus* is 5 wt % based on the total weight of the pulverized product of the *Gryllus bimaculatus*.

7. A *Gryllus bimaculatus* extract prepared by the method of claim 1, wherein the *Gryllus bimaculatus* extract has a protein content of 40 wt % or more based on the total weight of solids of the *Gryllus bimaculatus* extract, wherein a polypeptide having a size of 500 Da or less and a free amino acid is included in a total content of 60 wt % or more based on the total weight of proteins contained in the *Gryllus bimaculatus* extract, and wherein the free amino acid content is 4.5 wt % or more based on the total weight of solids of the *Gryllus bimaculatus* extract.

8. The *Gryllus bimaculatus* extract of claim 7, wherein the *Gryllus bimaculatus* extract is in the form of a liquid, a gel, or a powder.

9. The *Gryllus bimaculatus* extract of claim 7, wherein the polypeptide having a size of 500 Da or less includes at least one selected from between a dipeptide and a tripeptide.

10. The *Gryllus bimaculatus* extract of claim 7, having a protein content of 45 wt % or more based on the total weight of solids of the *Gryllus bimaculatus* extract.

11. A food comprising the *Gryllus bimaculatus* extract of claim 7.

* * * * *